US012779234B2

(12) United States Patent
Doerr et al.

(10) Patent No.: US 12,779,234 B2
(45) Date of Patent: Nov. 3, 2026

(54) IMPLANTABLE CARDIOVERTER DEFIBRILLATOR DEVICE COMPRISING A SHOCK GENERATION CIRCUITRY WITH A CURRENT LIMITING CIRCUIT

(71) Applicant: BIOTRONIK SE & Co. KG, Berlin (DE)

(72) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 205 days.

(21) Appl. No.: 18/716,570

(22) PCT Filed: Dec. 6, 2022

(86) PCT No.: PCT/EP2022/084523
§ 371 (c)(1),
(2) Date: Jun. 5, 2024

(87) PCT Pub. No.: WO2023/110517
PCT Pub. Date: Jun. 22, 2023

(65) Prior Publication Data

US 2025/0032812 A1 Jan. 30, 2025

(30) Foreign Application Priority Data

Dec. 16, 2021 (EP) .................................... 21215005

(51) Int. Cl.
*A61N 1/39* (2006.01)
*A61N 1/02* (2006.01)
*A61N 1/05* (2006.01)

(52) U.S. Cl.
CPC ........... *A61N 1/3956* (2013.01); *A61N 1/025* (2013.01); *A61N 1/0563* (2013.01); *A61N 1/3987* (2013.01)

(58) Field of Classification Search
None
See application file for complete search history.

(56) References Cited

U.S. PATENT DOCUMENTS 5,662,698 A * 9/1997 Altman .................. A61N 1/056
607/123
5,824,017 A * 10/1998 Sullivan ............... A61N 1/3904
607/5
(Continued)

OTHER PUBLICATIONS

Extended European Search Report mailed Jun. 1, 2022, by the European Patent Office for corresponding Application No. EP21215005.6. (8 pages).

(Continued)

*Primary Examiner* — Manolis Pahakis
(74) *Attorney, Agent, or Firm* — Buchanan Ingersoll & Rooney PC

(57) ABSTRACT

An implantable cardioverter defibrillator device comprises a generator device having a processing circuitry and a shock generation circuitry, and at least one lead comprising a shock electrode for emitting an electrical output pulse. The shock generation circuitry comprises an energy supply arrangement containing at least one energy storage device for supplying energy to form an output pulse, an output circuit for outputting said output pulse to the shock electrode, and a current limiting circuit arranged electrically in between the energy supply arrangement and the output circuit such that a current supplied from the energy supply arrangement flows through the current limiting circuit towards the output circuit. The current limiting circuit comprises at least one current limiting component, wherein the current limiting circuit is controllable by the processing circuitry to modulate a current flowing through the current limiting circuit.

14 Claims, 7 Drawing Sheets

(56) References Cited

U.S. PATENT DOCUMENTS

| | | | | |
|---|---|---|---|---|
| 5,906,633 | A * | 5/1999 | Mouchawar | A61N 1/3956 607/63 |
| 6,647,294 | B2 | 11/2003 | Vane et al. | |
| 6,963,773 | B2 * | 11/2005 | Waltman | A61N 1/39 607/4 |
| 7,386,342 | B1 | 6/2008 | Falkenberg et al. | |
| 7,986,992 | B2 | 7/2011 | Ideker et al. | |
| 8,209,005 | B1 * | 6/2012 | Moulder | A61N 1/3925 607/17 |
| 8,423,137 | B2 * | 4/2013 | Moulder | A61N 1/3906 607/5 |
| 8,494,646 | B2 * | 7/2013 | Weiss | A61N 1/3718 607/59 |
| 8,560,066 | B2 | 10/2013 | Janardhan et al. | |
| 10,252,069 | B1 * | 4/2019 | Kroll | A61N 1/08 |
| 10,413,741 | B2 | 9/2019 | Efimov et al. | |
| 2003/0195569 | A1 | 10/2003 | Swerdlow et al. | |
| 2012/0158097 | A1 * | 6/2012 | Weiss | A61N 1/3718 607/59 |
| 2012/0179218 | A1 * | 7/2012 | Moulder | A61N 1/3906 607/5 |
| 2012/0190969 | A1 * | 7/2012 | Kameli | A61N 1/39624 607/29 |
| 2012/0209343 | A1 * | 8/2012 | Efimov | A61N 1/395 607/14 |
| 2014/0277244 | A1 * | 9/2014 | Rockweiler | A61N 1/3702 607/28 |
| 2015/0306406 | A1 | 10/2015 | Crutchfield et al. | |
| 2015/0306407 | A1 * | 10/2015 | Crutchfield | A61N 1/3912 607/5 |
| 2017/0157414 | A1 * | 6/2017 | Anderson | A61N 1/371 |
| 2018/0159322 | A1 * | 6/2018 | Zmuda | A61B 5/308 |
| 2019/0054297 | A1 * | 2/2019 | Zhang | A61N 1/36507 |
| 2019/0388685 | A1 * | 12/2019 | Doerr | A61B 5/0071 |
| 2020/0094058 | A1 * | 3/2020 | Mangual-Soto | A61B 5/349 |

OTHER PUBLICATIONS

International Search Report (PCT/ISA/210) and Written Opinion (PCT/ISA/237) mailed Jan. 30, 2023, by the European Patent Office as the International Searching Authority for International Application No. PCT/EP2022/084523. (12 pages).

* cited by examiner

IMPLANTABLE CARDIOVERTER DEFIBRILLATOR DEVICE COMPRISING A SHOCK GENERATION CIRCUITRY WITH A CURRENT LIMITING CIRCUIT

CROSS-REFERENCE TO RELATED APPLICATIONS

This application is the United States National Phase under 35 U.S.C. § 371 of PCT International Patent Application No. PCT/EP2022/084523, filed on Dec. 6, 2022, which claims the benefit of European Patent Application No. 21215005.6, filed on Dec. 16, 2021, the disclosures of which are hereby incorporated by reference herein in their entireties.

TECHNICAL FIELD

The instant invention concerns an implantable cardioverter defibrillator device and a method for operating an implantable cardioverter defibrillator device.

BACKGROUND

An implantable cardioverter defibrillator device generally comprises a generator device comprising a processing circuitry and a shock generation circuitry. The implantable cardioverter defibrillator device in addition comprises at least one lead comprising a shock electrode for emitting an electrical output pulse.

The implantable cardioverter defibrillator device in particular is designed for emitting electrical shocks in case life-threatening arrhythmias of a patient's heart are detected. By means of an electrical shock a defibrillation shall be achieved in order to reset the cardiac rhythm back to a normal state.

When implanting an cardioverter defibrillator device it is required to establish whether the cardioverter defibrillator device has been implanted such that it reliably may sense cardiac signals and may couple energy into the patient's heart in order to achieve a desired action. For this, typically a so-called threshold testing in the context of the implantation procedure is performed in order to evaluate whether a detected arrhythmia may be effectively ended by emission of a shock pulse using the cardioverter defibrillator device. For such a threshold testing, it is desirous to cause the patient's heart to enter into a fibrillation state. In the fibrillation state, a sensitivity of a sensing arrangement of the cardioverter defibrillator device may be tested, and the effectiveness of a coupling of the shock electrode may be assessed in order to potentially adapt the positioning of sensing electrodes as well as the shock electrode and to configure the setup of the cardioverter defibrillator device for its subsequent operation.

In an apparatus and method disclosed in U.S. Publication No. 2015/0306406 A1 an injection waveform for performing a threshold testing in an implantable medical device is generated such that tests may be performed during the implant procedure or during a device checking procedure. The threshold test may include induction of an arrhythmia, such as ventricular fibrillation, followed by the delivery of therapy at various progressively increasing stimulation parameters to terminate the arrhythmia. The induction of the arrhythmia may be accomplished via a delivery of a relatively low energy shock or through the delivery of an induction stimulation pulse to the cardiac tissue timed concurrently with the vulnerable phase of the cardiac cycle.

U.S. Publication No. 2003/0195569 A1 discloses a method for determining a cardiac shock strength, for example a programmed first therapeutic shock strength of an implantable cardioverter defibrillator, including sensing a change in a T wave of an electrogram with respect to time, delivering a test shock by delivering a test shock at a test shock strength and at a test shock time relating to a maximum of a first derivative of the T wave with respect to time, and sensing for cardiac fibrillation. The implantable cardioverter defibrillator herein is designed for a transvenous implantation.

Another implantable cardioverter defibrillator device is disclosed, for example, in U.S. Pat. No. 7,386,342.

For producing an output pulse, for example a fibrillation pulse to induce a fibrillation state, an implantable cardioverter defibrillator device may use the shock generation circuitry which also is employed when producing a shock pulse for achieving a defibrillation action. When using the same circuitry for producing the fibrillation pulse and a defibrillation pulse, care must be taken that the production of the fibrillation pulse in a corresponding circuitry does not interfere with the production of a shock pulse for achieving a defibrillation action.

The present disclosure is directed toward overcoming one or more of the above-mentioned problems, though not necessarily limited to embodiments that do.

SUMMARY

It is an object of the instant invention to provide an implantable cardioverter defibrillator device and a method for operating an implantable cardioverter defibrillator device which allow in an easy and efficient way to produce different kinds of output pulses, in particular for inducing a fibrillation state as well as for achieving a defibrillation action, by employing the same shock generation circuitry.

In one aspect, an implantable cardioverter defibrillator device comprises a generator device comprising a processing circuitry and a shock generation circuitry, and at least one lead comprising a shock electrode for emitting an electrical output pulse. The shock generation circuitry comprises an energy supply arrangement containing at least one energy storage device for supplying energy to form an output pulse, an output circuit for outputting the output pulse to the shock electrode and a current limiting circuit arranged electrically in between the energy supply arrangement and the output circuit such that a current supplied from the energy supply arrangement flows through the current limiting circuit towards the output circuit. The current limiting circuit comprises at least one current limiting component. The current limiting circuit is controllable by the processing circuitry to modulate a current flowing through the current limiting circuit.

The implantable cardioverter defibrillator device comprises a shock generation circuitry which comprises an energy supply arrangement, an output circuit and a current limiting circuit. The energy supply arrangement is formed by one or a multiplicity of energy storage devices, for example capacitors, which may be caused to discharge in order to supply energy to form output pulses. The energy supply arrangement is electrically connected to the output circuit via a current limiting circuit, such that a current flows from the energy supply arrangement to the output circuit via the current limiting circuit.

The current limiting circuit is designed to limit a current flowing to the output circuit. For this, the current limiting circuit comprises a current limiting component which is controlled by the processing circuitry of the generator device in order to perform a modulation of the current flowing through the current limiting circuit. The modulation in particular may be a pulse width modulation (PWM), with a modulation depth between, for example, 25% to 100% (100% corresponding to a 0 amplitude in between pulses). In that the current limiting circuit limits the current flowing to the output circuit and hence limits the power of an output pulse fed by means of the output circuit to the shock electrode, an output pulse may be generated which comprises a reduced voltage level and a reduced power and hence may be suitable for inducing a cardiac functional state with limited impact on a patient. By means of an output pulse exhibiting a reduced voltage level and a reduced power in particular a fibrillation state may be induced, the output pulse for inducing the fibrillation state having a reduced voltage level and a reduced power in particular in comparison to a shock pulse used for performing a defibrillation action for resetting a tachycardic heart rhythm to a regular sinus rhythm.

The current limiting component serves to reduce and hence limit the amplitude of a current flowing through a conduction path in which the current limiting component is arranged. The limiting effect of the current limiting component may be controlled, in that, for example, a resistance value of the current limiting component may be controlled, or the current limiting component may be selectively activated (such that a current flows through the current limiting component) or deactivated (such that the current does not flow through the current limiting component).

By using the current limiting circuit, a power and voltage level of an output pulse may be controlled such that an excessive voltage level and power is avoided, while producing pulses of sufficient energy to induce a particular cardiac state. By means of the current limiting circuit a control means in between the energy supply arrangement and the output circuit is provided, which may allow for an easy and effective control and hence a reliable operation of the shock generation circuitry.

In that the current limiting circuit is arranged electrically in between the energy supply arrangement and the output circuit, a single current limiting circuit may be used for controlling a current flow to the output circuit. The current limiting circuit is arranged in an electrical conduction path in between the energy supply arrangement and the output circuit such that a current from the energy supply arrangement flows through the current limiting circuit to the output circuit and is modulated by controlling the current limiting circuit.

The implantable cardioverter defibrillator device may in particular be a non-transvenous implantable cardioverter defibrillator device (in short non-transvenous ICD), which is designed for implantation external to a patient's heart. In a non-transvenous implantable cardioverter defibrillator device, a generator device may, for example, be implanted subcutaneously in a patient. A lead, in a connected state, extends from the generator device, the lead being implanted such that it fully rests outside of the patient's heart. The lead may, for example, extend from the generator device towards a location in the region of the patient's sternum, the shock electrode hence being placed outside of the patient's heart for emitting an electrical shock pulse at a location external to the patient's heart.

The term "non-transvenous" in this respect in particular shall express that the lead of the non-transvenous implantable cardioverter defibrillator device does not extend transvenously into the heart, but fully rests outside of the patient's heart.

In another embodiment, the implantable cardioverter defibrillator device may be designed for a transvenous implantation, i.e., by implanting a lead to extend transvenously into the heart.

The implantable cardioverter defibrillator device generally is configured to emit a shock pulse for achieving a defibrillation. The implantable cardioverter defibrillator device may serve for monitoring and treating potentially life-threatening arrhythmias of a patient's heart. If the implantable cardioverter defibrillator device is a non-transvenous implantable cardioverter defibrillator device, the shock electrode in an implanted state of the defibrillator device is placed outside of the heart of the patient, for example in the region of the sternum of the patient, such that a shock pulse for achieving a defibrillation is generated outside of the heart.

In one embodiment, the processing circuitry is configured to control the current limiting circuit to generate a fibrillation pulse for emission by the shock electrode in order to induce a cardiac fibrillation state or to generate a defibrillation pulse for emission by the shock electrode in order to terminate a cardiac fibrillation state. The shock generation circuitry may be configured to produce fibrillation pulses producing a fibrillation state and defibrillation pulses for performing a defibrillation action. The current limiting circuit herein may be involved for producing a fibrillation pulse and/or for producing a defibrillation pulse. In one embodiment, the current limiting circuit is active for producing a fibrillation pulse such that a current for producing the fibrillation pulse is manipulated by the current limiting circuit, whereas the current limiting circuit is not active for producing a defibrillation pulse. In another embodiment, the current limiting circuit is active for producing a defibrillation pulse, but is not active for producing the fibrillation pulse. In yet another embodiment, the current limiting circuit is active for producing both a fibrillation pulse and a defibrillation pulse.

In one embodiment, the processing circuitry is configured to control the current limiting circuit to modulate the current flowing through the current limiting circuit to generate the fibrillation pulse according to a first modulation scheme and to generate a defibrillation pulse for emission by the shock electrode according to a second modulation scheme different than the first modulation scheme. A current for producing a fibrillation pulse as well as for producing a defibrillation pulse hence flows through and is modulated by the current limiting circuit. A modulation applied for producing the fibrillation pulse herein, however, is different than a modulation applied for producing the defibrillation pulse. In this way, in particular, a fibrillation pulse at a reduced power and reduced voltage level may be produced in comparison to a defibrillation pulse.

By using the current limiting circuit, in particular, an output pulse acting as a fibrillation pulse may be produced for inducing a fibrillation state. Subsequent to emitting a fibrillation pulse, it may be assessed whether the patient's heart has entered into a fibrillation state. If a fibrillation state is detected, for example a special testing may be performed. If it is found that the patient's heart has not entered into a fibrillation state, another fibrillation pulse may be emitted, wherein parameters for the next fibrillation pulse may be adapted, for example by increasing its voltage level and/or its energy. The adaption of the fibrillation pulse may be performed automatically by the system. Alternatively, a user may be prompted to program or confirm the parameters for the fibrillation pulse, wherein the system may propose changes for confirmation by the user. The emission of fibrillation pulses may be repeated until a fibrillation state is successfully detected. A user may be enabled to terminate the emission of the fibrillation pulses.

Subsequent to entering the fibrillation state, a threshold testing may be performed. Generally, during the threshold testing a positioning of the lead with the shock electrode and potentially other electrode poles arranged thereon may be tested. In addition, a general setup of the implantable cardioverter defibrillator device may be adapted in order to achieve an effective defibrillation during subsequent operation of the non-transvenous implantable cardioverter defibrillator device. During the threshold testing, for example, the device's capability of detecting and terminating an arrhythmia may be assessed.

In one embodiment, the output circuit is formed by an H bridge comprising switches to selectively form conduction paths for outputting the output pulse in a first polarity or in a second, opposite polarity. In the H bridge, for example four switches may be used, wherein a first conduction path may be formed by a first pair of switches to connect terminals of the H bridge circuit to inject an output pulse into the patient at a first polarity, and a second conduction path may be formed by a second pair of switches to connect the terminals of the H bridge to inject an output pulse of a second, opposite polarity into the patient. By selectively switching the switches, the connection paths may be selectively opened or closed in order to selectively output an output pulse of a particular polarity.

In one embodiment, the shock generation circuitry comprises a multiplicity of energy storage devices, for example in the shape of capacitors, functionally connected to at least one switching device. The processing circuitry herein is configured to control the at least one switching device to supply energy for generating the output pulse using all of the multiplicity of energy storage devices or a combination of some of the multiplicity of energy storage devices. The output pulse in particular may be produced by causing energy storage devices in the shape of capacitors to discharge.

The shock generation circuitry herein may be controlled to produce an output pulse which is shaped as a rectangular or approximately rectangular pulse. Alternatively, the output pulse may be shaped to exhibit a rising ramp.

The output pulse, such as a fibrillation pulse, may have a duration between 0.5 ms to 50 ms.

The output pulse, such as a fibrillation pulse, may have an energy in between 1 J to 50 J.

The output pulse, such as a fibrillation pulse, may have a maximum voltage in a range between 5 V to 800 V.

In one embodiment, the processing circuitry is configured to control the current limiting circuit to set an effective voltage level of the output pulse using a pulse width modulation. In particular, the processing circuitry may control the current limiting circuit such that a sequence (burst) of pulses is produced to form the output pulse. A modulation depth may be in a range between 25% to 100%. If a modulation depth of 100% is employed, pulses are selectively switched on and off by controlling the current limiting circuit. If a modulation depth less than 100% is used, the current limiting component may be switched between different resistance values such that pulses of varying amplitude are generated for producing the output pulse.

By controlling the current limiting circuit, pulses of varying widths and at varying distances may be produced. The pulse width may, in one embodiment, be time-controlled. In another embodiment, the pulse width may be voltage-controlled. In a preferred embodiment, at least the majority (>50%, >80%>95%) of the provided pulses shall guaranty a desired effectiveness. According to electro-physiology the effectiveness is governed by an electrical charge dose provided by the pulse. The electrical charge dose results from the integral over time of the electrical current provided by the pulse. The current is a result of the pulse voltage driving charge through the living body resistance. To control the electrical charge dose, hence, the pulse width may be controlled. Because an available voltage level provided by the energy supply arrangement decreases during application due to a discharging of capacitors, the pulse width may be adapted accordingly.

Another way to control effectiveness is to adapt a total duration of the pulse train. If there is an increased charge loss during one pulse due to a lower body resistance, the distance in between subsequent pulses may be increased in order to stretch the pulse train to obtain effective outputs (sufficient charge per pulse) over a sufficiently long duration. The duration of the pulse train is programmable in one embodiment.

In another embodiment, the pulse width is set based on the peak voltage of the instant pulse itself or the peak voltage of at least one prior pulse. According to one embodiment the width calculation is based on an extrapolation of the progression of prior pulse peak voltages (optionally including the peak voltage of the instant pulse which has just started). The extrapolation may be performed by applying a linear or exponential extrapolation. In one embodiment, the pulse width is set based on a voltage decay that occurs during a pulse.

In one embodiment, the at least one current limiting component comprises a resistance, an inductance, or a semiconductor component. A semiconductor component for providing for a current limiting may, for example, be a current limiting diode. The current limiting component may be a passive component or an active current limiting arrangement including active and passive elements such as transistors and resistors.

The current limiting component may be controllable, for example to control a resistance value of the current limiting component.

In one embodiment, the current limiting circuit comprises a controllable component which is controllable by the processing circuitry. The controllable component may, for example, be a switch, such as a semiconductor switch, for example a transistor such as an FET, an IGBT or an AGT. The controllable component may in particular be controlled by the processing circuitry in order to selectively open and close a conduction path in which the current limiting component is arranged such that the current limiting opponent may be selectively activated or deactivated.

In one embodiment, the current limiting circuit comprises a switch, wherein the current limiting component is arranged in a first path and the switch is arranged in a second path electrically in parallel to the first path. By controlling the switch, for example using the processing circuitry, current may be supplied via the first path or the second path. If the switch is closed, current (predominantly) flows through the second path and hence not through the current limiting component. If the switch is opened, current flows through the current limiting component in the first path. The current limiting component in addition may be controllable in order to modulate the current flowing through the current limiting component.

For controlling the current limiting circuit, a driver may be used which functions at floating potential on its secondary side. Floating potential means that there is no galvanic connection between the primary and the secondary side. Such driver functioning at floating potential on its secondary side is used to control, e.g., an arrangement of switches. By use of such a driver the processing circuitry can be implemented using low voltage electronics. Low voltage electronics may use a voltage level as supplied directly from a battery. The battery voltage may be in the range of 1.5 V to 15 V, for example at 3 V, 6 V or 9 V. Switches in turn may operate at voltage levels dictated by the energy supply arrangement. While the processing circuitry generates commands for actuating the switches, the driver translates the commands to a secondary side electrical potential completely isolated from a primary side electrical potential. The translation is done, for example, by means of optical radiation, magnetic induction, or mechanic transmission (also including vibrations, including acoustics). In a preferred implementation the driver may, for example, be an optocoupler. Another option for a driver may be an inductively coupled high-side driver.

A resistor of the current limiting circuit may be used as a dump resistor for draining off energy which is not used for producing an output pulse. The resistor may, for example, comprise an intermediate terminal (e.g., realized as a series connection of two resistors) such that, e.g., only a portion of the resistor is used as a limiting resistance for the current limiting, whereas the entire resistor may be used for draining off energy (dumping).

In one embodiment the implantable cardioverter defibrillator device comprises a sensing arrangement for sensing electrocardiogram signals. Sensed signals are forwarded to the processing circuitry, which processes the signals in order to, e.g., identify a ventricular contraction event in a sensed electrocardiogram signal. Based on a sensed cardiac activity, then, an output pulse such as a fibrillation pulse may be generated.

The sensing arrangement may comprise multiple electrode poles. One or multiple electrode poles of the sensing arrangement herein may be placed on the lead carrying the shock electrode. For example, one electrode pole may be placed on the lead at a position proximal to the shock electrode. Another electrode pole may be placed on the lead at a position distal to the shock electrode.

Further electrode poles may be placed on further leads connected to the generator device. Alternatively or in addition, one or multiple electrode poles may be formed by a housing of the generator device. Yet alternatively or in addition, the shock electrode may be used as a sense electrode pole for sensing electrocardiogram signals.

In one embodiment, the sensing arrangement comprises three or more electrode poles. The three or more electrode poles form multiple pairs of electrode poles which may be used for sensing electrocardiogram signals. The different pairs span sense vectors which, each by itself, may be used to sense an electrocardiogram signal. The different sense vectors herein may exhibit a different spatial sensitivity with respect to electrocardiogram signals and hence may be used to sense information in a multichannel processing. Signals received by means of the different sense vectors as spanned by different pairs of electrode poles may be combined in order to sense ventricular activity and to derive information from electrocardiogram signals.

In one embodiment, the processing circuitry is configured to identify ventricular contraction events in an electrocardiogram signal to determine a timing of a fibrillation pulse.

Ventricular contraction events may be sensed in electrocardiogram signals of one or of multiple signal vectors as spanned by one or multiple pairs of electrode poles. Information from multiple signals received by multiple pairs of electrode poles spanning different sense vectors may in particular be combined in order to reliably detect ventricular contraction events in electrocardiogram signals.

An output pulse may exhibit a single phase. An output pulse may, in another embodiment, exhibit multiple phases. Within the multiple phases polarities of the pulse may change.

The generator device may have a volume smaller than 70 $cm^3$.

The implantable cardioverter defibrillator device may be MRI compatible.

The implantable cardioverter defibrillator device may comprise a communication interface for communicating with an external device, for example within a home-monitoring system. The communication interface may, for example, employ a common communication scheme such as a MICS communication or a BLE communication.

In another aspect, in a method for operating an implantable cardioverter defibrillator device the implantable cardioverter defibrillator device comprises a generator device and at least one lead having a shock electrode for emitting an output pulse. The method comprises: supplying, using an energy supply arrangement containing at least one energy storage device of a shock generation circuitry of the generator device, energy to form an output pulse; outputting, using an output circuit of said shock generation circuitry, said output pulse to the shock electrode; and controlling, using a processing circuitry of the generator device, a current limiting circuit comprising at least one current limiting component to modulate a current flowing through the current limiting circuit, wherein the current limiting circuit is arranged electrically in between the energy supply arrangement and the output circuit such that a current supplied from the energy supply arrangement flows through the current limiting circuit towards the output circuit.

The advantages and advantageous embodiments described above for the implantable cardioverter defibrillator device equally apply also to the method, such that it shall be referred to the above in this respect.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The idea of the present invention shall subsequently be described in more detail with reference to the embodiments as shown in the drawings. Herein.

DETAILED DESCRIPTION

Figure 1:
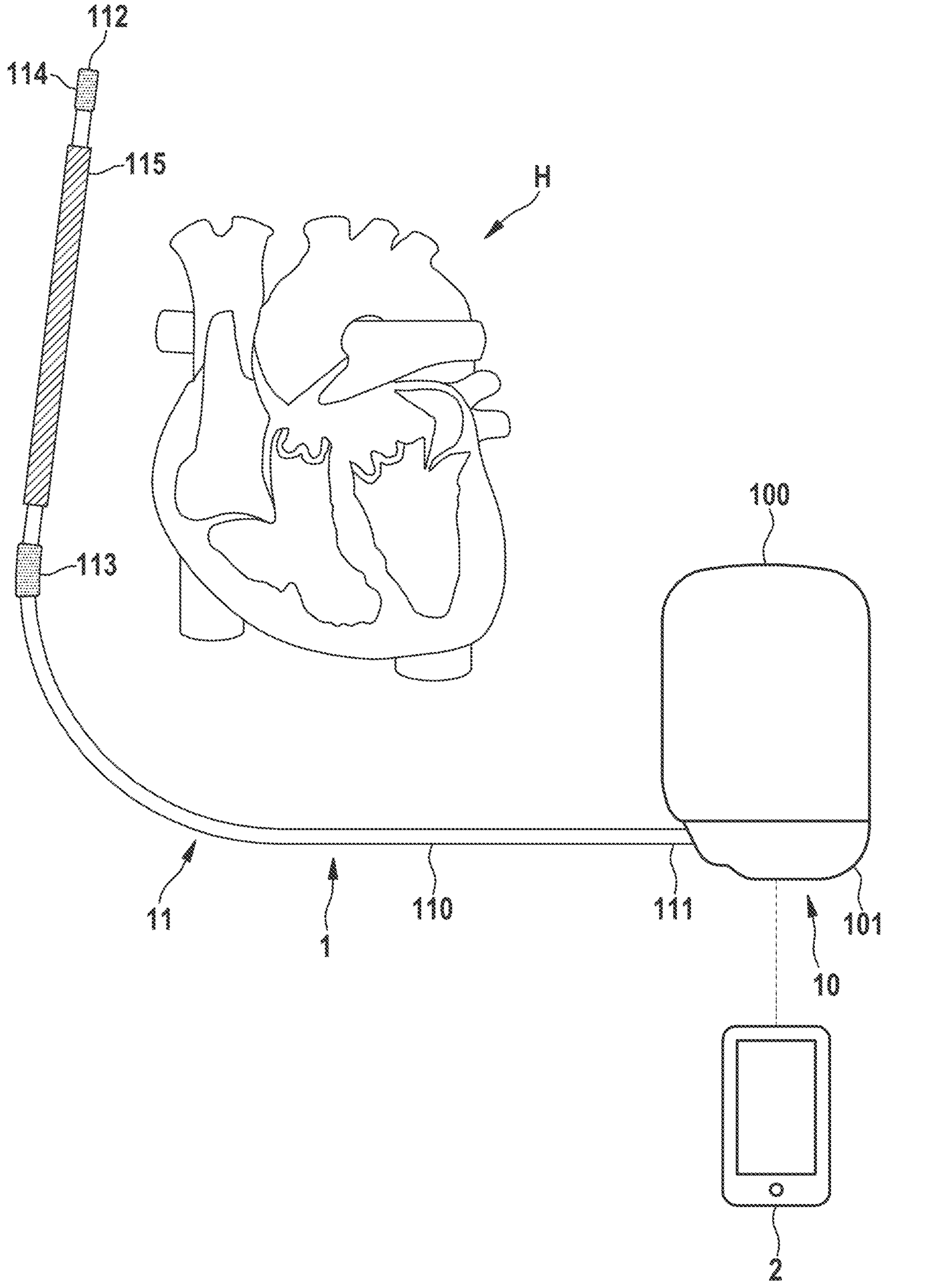
FIG. 1 shows a schematic drawing of an implantable cardioverter defibrillator device in an implanted state in a patient.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

Referring to FIG. 1, in a setup of a therapy system an implantable cardioverter defibrillator device 1 is designed as a non-transvenous implantable cardioverter defibrillator device 1. The non-transvenous implantable cardioverter defibrillator device 1 is implanted such that the implantable cardioverter defibrillator device 1 is completely external to the heart H, the implantable cardioverter defibrillator device 1 comprising a generator device 10 encapsulated within a housing 100, and a lead 11 connected to the generator device 10 at a proximal end 111 and carrying electrode poles 113, 114 as well as a shock electrode 115 in the shape of a coil formed on a distal portion close to a distal end 112 of the lead 11. The electrode poles 113, 114, for example formed as ring electrodes on either side of the shock electrode 115, serve to sense cardiac signals for processing within the generator device 10 of the implantable cardioverter defibrillator device 1, such that based on sensed signals an arrhythmia may be identified and a shock pulse may be generated for providing for a defibrillation therapy.

The implantable cardioverter defibrillator device 1, in the embodiment of FIG. 1, is designed for a non-transvenous implantation, that is an implantation external to the patient's heart H. In particular, the lead 11 connected to the generator device 10 shall rest outside of the patient's heart H and shall not extend transvenously into the heart, the shock electrode 115 hence, in an implanted state, being placed outside of the heart H for providing for a defibrillation therapy.

For example, the generator device 10 may be implanted subcutaneously in a patient. The lead 11, with a lead body 110, may extend from the generator device 10 towards the sternum of the patient, the lead 11, for example, tunneling through tissue in the region of the sternum and being placed beneath the sternum of the patient.

The implantable cardioverter defibrillator device 1 may comprise a communication interface for communicating with an external device 2, for example within a home-monitoring system.

Figure 2:
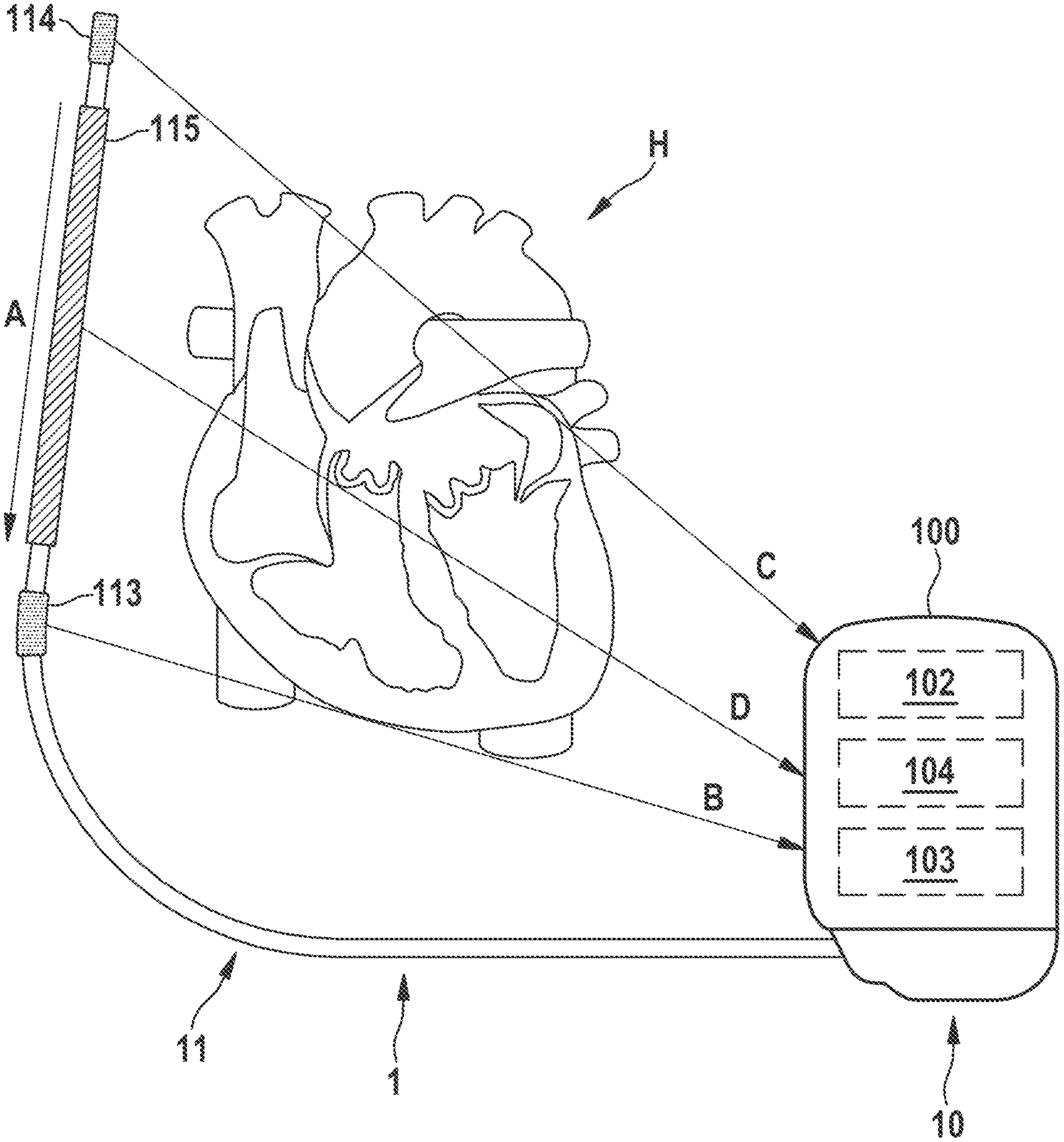
FIG. 2 shows the cardioverter defibrillator device of FIG. 1, illustrating sense vectors spanned by different pairs of electrode poles of a sensing arrangement of the device.

Referring now to FIG. 2, the generator device 10 generally comprises a processing circuitry 102 for controlling operation of the implantable cardioverter defibrillator device 1. In addition, the generator device 10 comprises a shock generation circuitry 103 and an energy storage 104, in particular in the shape of a battery.

The processing circuitry 102 in particular serves to process signals sensed via a sensing arrangement formed by the electrode poles 113, 114 arranged on the lead 11 and additional poles, such as the shock electrode 115 and the housing 100 of the generator device 10. The different poles of the sensing arrangement form pairs of electrode poles in between which sense vectors A, B, C, D are spanned, as illustrated in FIG. 2, the different sense vectors A, B, C, D allowing to sense electrocardiogram signals from the patient's heart H with a different spatial sensitivity, hence allowing to sense and process information from the patient's heart H in a multichannel processing.

The implantable cardioverter defibrillator device 1 as shown in FIGS. 1 and 2 in particular shall be configured to perform a defibrillation therapy. Herein, upon implantation of the implantable cardioverter defibrillator device 1 it shall be assessed whether the implantable cardioverter defibrillator device 1 is enabled for operation by employing a so-called threshold testing. Within the threshold testing it in particular is checked whether, using the implantable cardioverter defibrillator device 1, an arrhythmia may reliably be detected, and a defibrillation therapy may be performed in order to overcome the arrhythmia.

For performing the threshold testing, the patient's heart H shall be set into a fibrillation state in which the patient's heart H exhibits a tachycardic fibrillation. Once the patient's heart H is in the fibrillation state, it may be assessed whether the arrhythmia may be detected, and a therapy by delivering a defibrillation shock using the shock electrode 115 may be provided in order to end the arrhythmia.

For causing a transition of the patient's heart H into the fibrillation state, in an initial phase prior to actual operation or in a recalibration phase between periods of operation, the processing circuitry 102 shall cause the shock generation circuitry 103 to emit an output pulse serving as a fibrillation pulse using the shock electrode 115, the fibrillation pulse being designed to cause the patient's heart H to enter into the fibrillation state.

A fibrillation pulse herein is to be emitted with a specific timing, for example, with respect to a prior ventricular contraction event, such that the file fibrillation pulse preferably falls into a vulnerable phase during the cardiac cycle, that is immediately prior or during a rising flank of a T wave during the cardiac cycle. The timing of the fibrillation pulse may be determined by means of the sensing arrangement. For example, by employing one or multiple sense vectors A, B, C, D of one or multiple different pairs of electrode poles, events in an electrocardiogram signal may be sensed and identified using the processing circuitry 102 of the generator device 10, and based on sensed events it may be determined when a fibrillation pulse is to be emitted in order to reliably induce a fibrillation state.

A fibrillation pulse, if timed correctly to fall into the vulnerable phase during a cardiac cycle, generally may exhibit a reduced energy and may have a reduced voltage level in comparison to a shock pulse which is produced and emitted in order to achieve a defibrillation action. Herein, it nevertheless may be beneficial to use the same shock generation circuitry 103 of the generator device 10 in order to produce the fibrillation state, making it necessary however to ensure that the different functions of the shock generation circuitry 103 for producing a fibrillation pulse and for producing a defibrillation shock pulse do not interfere with each other.

Figure 3:
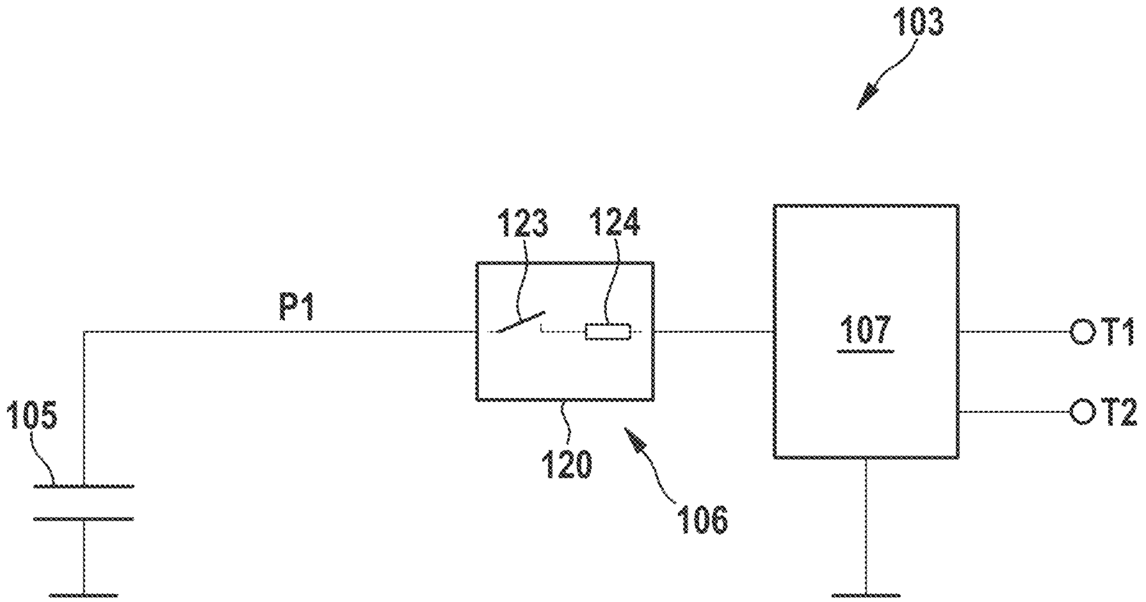
FIG. 3 shows a schematic drawing of an embodiment of a shock generation circuitry comprising an energy storage arrangement, a current limiting circuit and an output circuit.

Referring now to FIG. 3, in one embodiment a shock generation circuitry 103 comprises an energy supply arrangement 105 comprising one or multiple energy storage devices, for example in the shape of capacitors, a current limiting circuit 106 and an output circuit 107, for example in the shape of an H bridge comprising switches to selectively form therapeutic conduction paths via terminals T1, T2 for outputting an output pulse of a particular polarity into the body of the patient.

The current limiting circuit 106 comprises a current limiting component 120 having, for example a resistance 124 and a switch 123. The current limiting circuit 106 is arranged electrically in between the energy supply arrangement 105 and the output circuit 107, such that a current is supplied from the energy supply arrangement 105 to the output circuit 107 via the current limiting circuit 106.

The current limiting circuit 106 is controllable by the processing circuitry 102. In particular, by controlling the current limiting circuit 106 a current flow through the current limiting circuit 106 is modulated in order to produce an output pulse to be output by the output circuit 107.

The control of the output circuit 106 in particular may take place by controlling the switch 123 to assume an open or a closed state. Alternatively or in addition, the resistance 124 may be controllable such that a resistance value may be selectively adapted.

The processing circuitry 102 may in particular control the current limiting circuit 106 to apply a pulse width modulation to produce an output pulse. The pulse width modulation may be achieved by controlling the switch 123. Alternatively or in addition the resistance 124 may be controlled. The pulse width modulation may have a modulation depth, for example, between 25% to 100%.

The switch 123 may, for example, be a semiconductor switch, such as a transistor, for example an FET, IGBT, or AGT.

Figure 4:
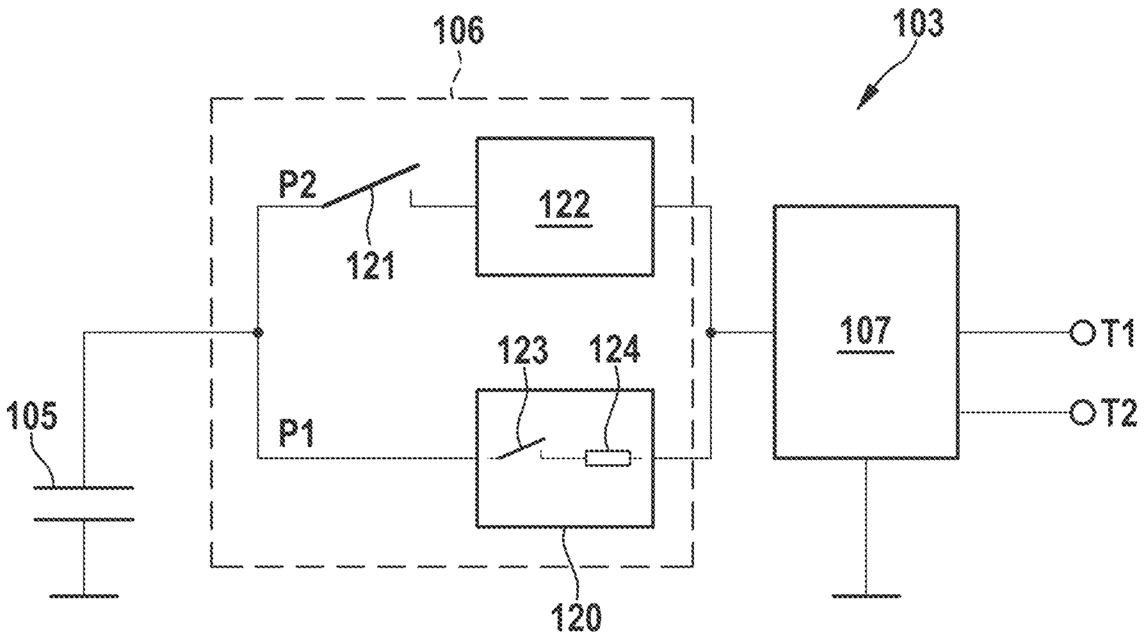
FIG. 4 shows another embodiment of a shock generation circuitry.

Referring now to FIG. 4, the current limiting circuit 106 may comprise two paths P1, P2, wherein in a first path P1 the current limiting component 120 is arranged and in the other, second path P2, in parallel to the first path P1, a switch 121 and a circuit component 122, for example a resistor, may be placed. By controlling the switch 121 a current may selectively flow via the first path P1 and hence via the current limiting component 120, or via the second path P2 and hence via the circuit component 122. In particular, when the switch 121 is opened, a current flows through the current limiting component 120. If instead the switch 121 is closed, a current predominantly flows via the circuit component 122 to the output circuit 107.

By means of the switch 121, hence, the current limiting component 120 may selectively be activated or deactivated. For example, by activating the current limiting component 120 an output pulse serving as a fibrillation pulse may be produced, the output pulse having a reduced voltage level and a reduced power. By deactivating the current limiting component 120, in turn, a shock pulse having an increased voltage level and an increased power may be produced, for example for performing a defibrillation action.

Figure 5:
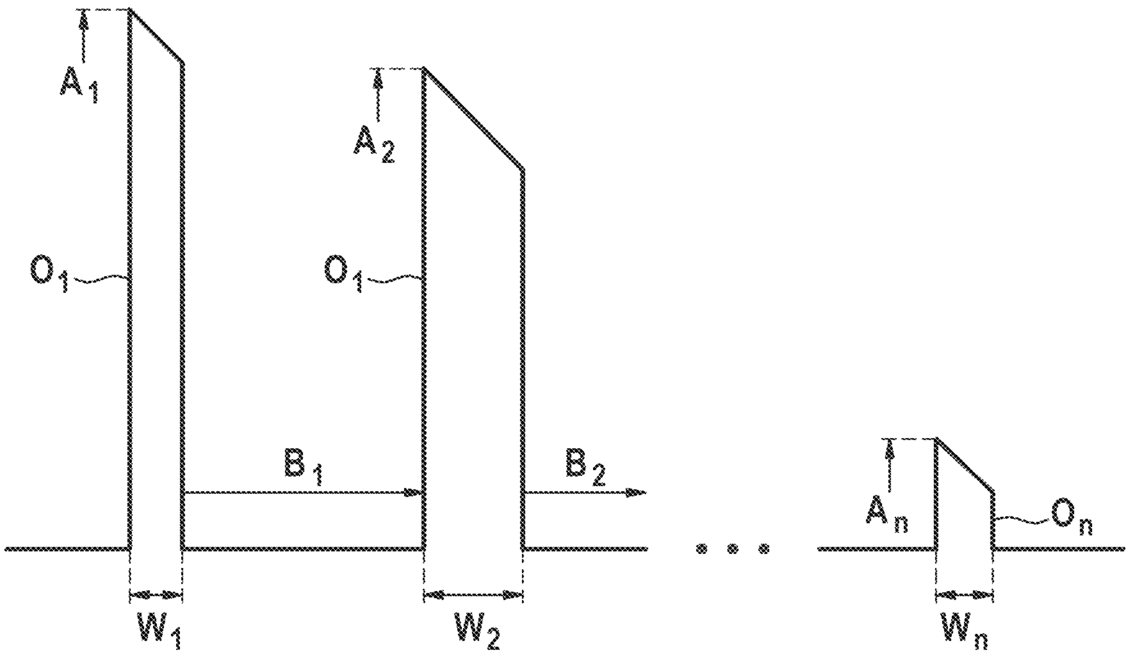
FIG. 5 shows an example of a sequence of pulses produced by a shock generation circuitry.

Referring now to FIG. 5, by using the current limiting circuit 106, in particular by supplying current through the current limiting component 120 and the resistor 124 arranged therein, a sequence of output pulses $O_1, O_2 \ldots O_n$ may be produced which are set to a desired pulse width $W_1$, $W_2$, $W_n$ and voltage level $A_1$, $A_2$, $A_n$. The pulses $O_1$, $O_2 \ldots O_n$ may differ in their pulse width $W_1$, $W_2$, $W_n$. Alternatively or in addition, a distance $B_1$, $B_2$ between neighboring pulses may vary. Yet alternatively or in addition, a maximum pulse amplitude $A_1$, $A_2$, $A_n$ may vary.

By modulating the pulse amplitude $A_1$, $A_2$, $A_n$, the pulse distance $B_1$, $B_2$ and the pulse width $W_1$, $W_2$, $W_n$, the effective power of a burst of pulses may be controlled by modulation in order to, for example, produce a fibrillation pulse.

The different output pulses $O_1, O_2 \ldots O_n$ may have an equal polarity, or may have a different polarity. By means of the H bridge the output pulses $O_1, O_2 \ldots O_n$ can be shaped as monophasic or biphasic pulses. The train of output pulses $O_1, O_2 \ldots O_n$ may comprise a mix of both monophasic and biphasic pulses.

As visible from FIG. 5, each pulse $O_1, O_2 \ldots O_n$ may exhibit a decaying ramp, due to a discharging of the energy supply arrangement 105, comprising, for example, an arrangement of capacitors, as shall be explained in more detail below with reference to FIGS. 6 to 8. In addition, the peak amplitude $A_1$, $A_2$, $A_n$ of a pulse $O_1, O_2 \ldots O_n$ in comparison to a prior pulse $O_1, O_2 \ldots O_n$ may be reduced, also due to a decaying charging level of the energy supply arrangement 105 during operation. The pulse width $W_1$, $W_2$, $W_n$ as well as the distance $B_1$, $B_2$ between neighboring pulses $O_1, O_2 \ldots O_n$ may be controlled, e.g., based on the peak voltage $A_1$, $A_2$, $A_n$ of a pulse $O_1, O_2 \ldots O_n$ or a prior pulse $O_1, O_2 \ldots O_n$ or based on a voltage level at the end of the pulse $O_1, O_2 \ldots O_n$ or a prior pulse $O_1, O_2 \ldots O_n$.

In the pulse train of FIG. 5, another way to control effectiveness may be to adapt a total duration of the pulse train. If there is an increased charge loss during one pulse due to a lower body resistance, the distance in between subsequent pulses may be increased in order to stretch the length of the pulse train to obtain effective outputs (sufficient charge per pulse) over a sufficiently long duration. The duration of the pulse train is programmable in one embodiment.

For example, the pulse width $W_1$, $W_2$, $W_n$ may be set based on an extrapolation of the progression of prior pulse peak voltages $A_1$, $A_2$, $A_n$ (optionally including the peak voltage of the instant pulse which has just started). The extrapolation may be performed by applying a linear or exponential extrapolation. In one embodiment, the pulse width $W_1$, $W_2$, $W_n$ is set based on a voltage decay that occurs during a pulse $O_1, O_2 \ldots O_n$.

Figure 6:
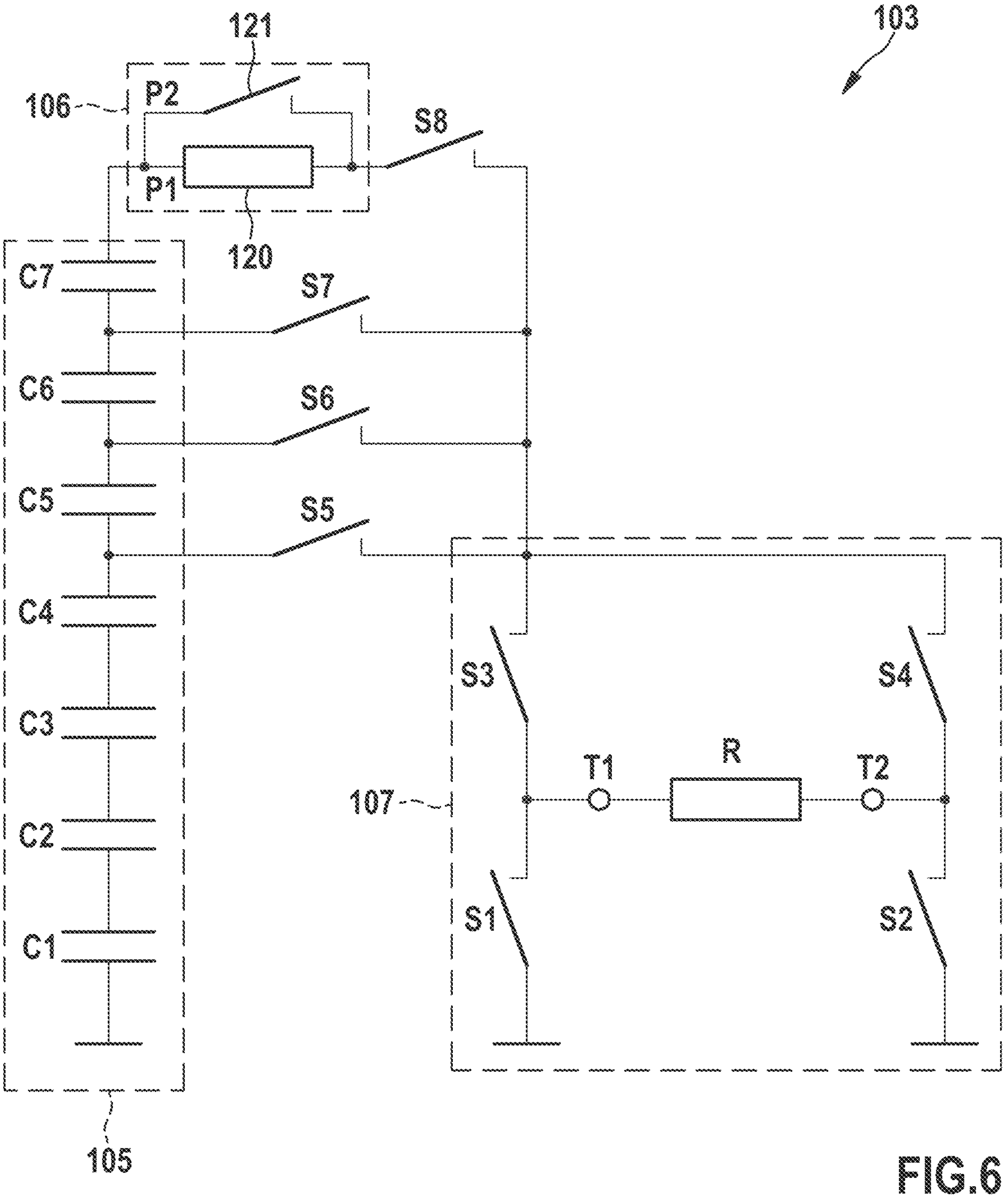
FIG. 6 shows an example of a shock generation circuitry for generating an output pulse, e.g., a fibrillation pulse.

Referring now to FIG. 6, the energy supply arrangement 105 may be implemented by an arrangement of energy storage devices formed by capacitors C1 to C7, which are functionally connected to an arrangement of switching devices S5 to S8. The capacitors C1 to C7 are in operative electrical connection to the energy storage 104, formed by a battery, of the generator device 10 and may be charged by the energy storage 104 in order to generate electrical pulses for emission by the shock electrode 115.

In the embodiment of FIG. 6, the capacitors C1 to C7 are connected to each other in an electrical series connection. Switching devices S5 to S8 selectively connect the capacitors C1 to C7 to an output circuit 107 formed by a so-called H bridge comprising switching devices S1 to S4. R represents an effective body impedance, the switching devices S1 to S4 selectively forming therapeutic current paths for emitting electrical pulses of a desired polarity into the patient's body.

By means of the switching devices S5 to S8 the electrical voltage of an electrical output pulse may be set. If only the switching device S5 is closed, the electrical pulse is formed by the charge of the capacitors C1 to C4, which discharge via the electrical path formed by the closed switching device S5. The electrical pulse is fed through the H bridge, wherein either the combination of switching devices S3, S2 or the combination of switching devices S4, S1 is closed in order to form an electrical pulse at a particular polarity for emission into the body of the patient.

In order to set the voltage level of the electrical pulse, either one of the switching devices S5 to S8 is closed. If the switching device S6 instead of the switching device S5 is closed, the electrical pulse is formed by discharging the combination of the capacitors C1 to C5. If instead the switching device S7 is closed, the charge of the capacitor C6 is added. If the switching device S8 is closed, the electrical pulse is formed by the combination of all capacitors C1 to C7.

By combining all capacitors C1 to C7 by closing (only) the switching device S8, a maximum voltage for the electrical pulse may be set.

In one embodiment, an output pulse, for example, serving as a fibrillation pulse is formed by the combination of all capacitors C1 to C7 by closing the switching device S8 (and leaving the switching devices S5 to S7 open). For forming the fibrillation pulse, herein, the capacitors C1 to C7 are charged by the energy storage 104 of the generator device 10 to such a level that the voltage of the fibrillation pulse is set to a desired level.

Herein, as visible in FIG. 6, in the electrical conduction path formed by the switch S8 a current limiting circuit 106 is arranged, such that when the switch S8 is closed the current is supplied from the energy supply arrangement 105 via the current limiting circuit 106 to the output circuit 107. The current limiting circuit 106 herein comprises a current limiting component 120, for example including a resistance 124 and a controllable component 123, for example a switch, as explained above in accordance with the embodiments of FIGS. 3 and 4. The current limiting component 120 is arranged in a first path P1, wherein in a second path P2 in parallel to the first path P1 a switch 121 is arranged for selectively activating or deactivating the current limiting component 120. In particular, when the switch 121 is opened, current is supplied via the current limiting component 120 to the output circuit 107. If instead the switch 121 is closed, current flows predominantly via the second path P2 and hence does not flow through the current limiting component 120 to the output circuit 107.

By means of the current limiting circuit 106 a current as supplied from the energy supply arrangement 105 may be limited, such that an excessive pulse amplitude is avoided. The output pulse herein is designed by modulation by controlling the current limiting circuit 106 using the processing circuitry 102.

Figure 7:
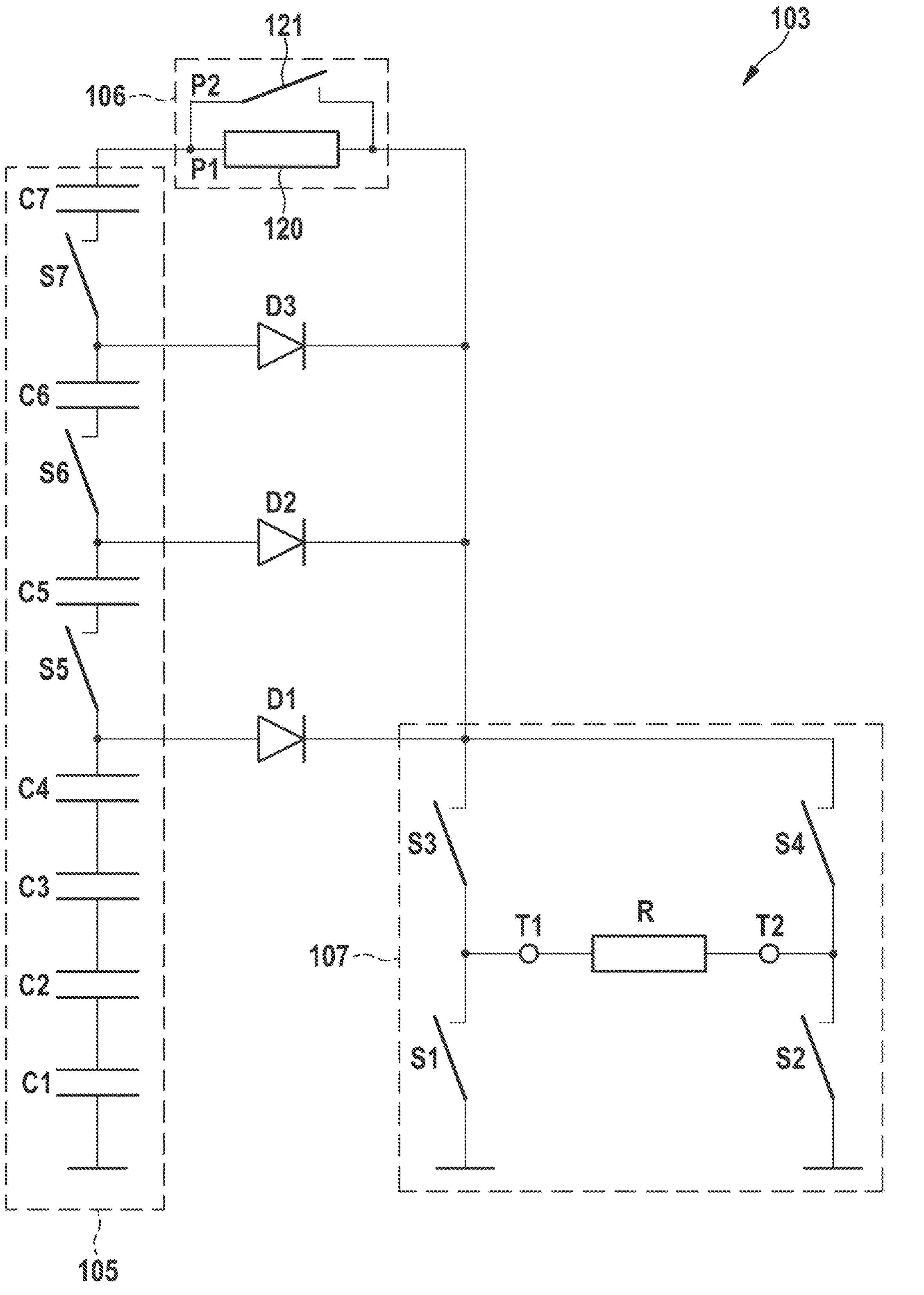
FIG. 7 shows another example of a shock generation circuitry for generating an output pulse, e.g., a fibrillation pulse.

Referring now to FIG. 7, in another embodiment the energy supply arrangement 105 comprises energy storage devices in the shape of capacitors C1 to C7, which each may be charged with electrical energy supplied from the energy storage 104 (FIG. 2) in the shape of a battery. The shock generation circuitry 103 in addition comprises switching devices S5-S7, which serve to selectively couple the energy storage devices C1 to C7 to an output circuit 107 in the shape of an H bridge comprising switching devices S1 to S4 for selectively forming a therapeutic current path via an associated diode D1-D3 for injecting a shock pulse into a patient, represented in the schematic circuit diagram of FIG. 7 by an effective body impedance R.

In the embodiment of FIG. 7, electrical pulses may be formed by selectively switching the switching devices S5 to S7 to a closed position. Herein, if all switching devices S5 to S7 are open, an electrical pulse is formed by the combination of the capacitors C1 to C4. By closing the switching device S5, the capacitor C5 is added to the combination, such that an electrical pulse is formed by discharging the combination of the capacitors C1 to C5. By closing also the switching device S6, the capacitor C6 is added. By closing all switching devices S5 to S7, an electrical pulse of a maximum voltage level is produced from the combination of all capacitors C1 to C7 along the electrical conduction path via diode D3 towards the output circuit 107 formed by the switching devices S1 to S4.

By combining all capacitors C1 to C7 by closing all switching devices S5 to S7, hence, a maximum voltage for the electrical pulse may be set. An output pulse, such as a fibrillation pulse, may be formed by the combination of all capacitors C1 to C7 by closing the switching devices S5 to S7. The capacitors C1 to C7 may be charged by the energy storage 104 of the generator device 10 to such a level that the voltage of the fibrillation pulse is set to a desired level.

In the embodiment of FIG. 7, a current limiting circuit 106 is arranged in the conduction path linked to capacitor C7 such that, when the switch S7 is closed, current flows through the current limiting circuit 106. Again, as described above in connection with the embodiment of FIG. 6, the current limiting circuit 106 comprises a current limiting component 120 in a first path P1 and a switch 121 in a second path P2 in parallel to the first path P1. By controlling the switch 121 using the processing circuitry 102 the current limiting component 120 may selectively be activated or deactivated in order to limit a current flowing to the output circuit 107 or not.

In addition, it shall be referred to the description in relation to the embodiment of FIG. 6 and the embodiments of FIGS. 3 and 4.

Figure 8:
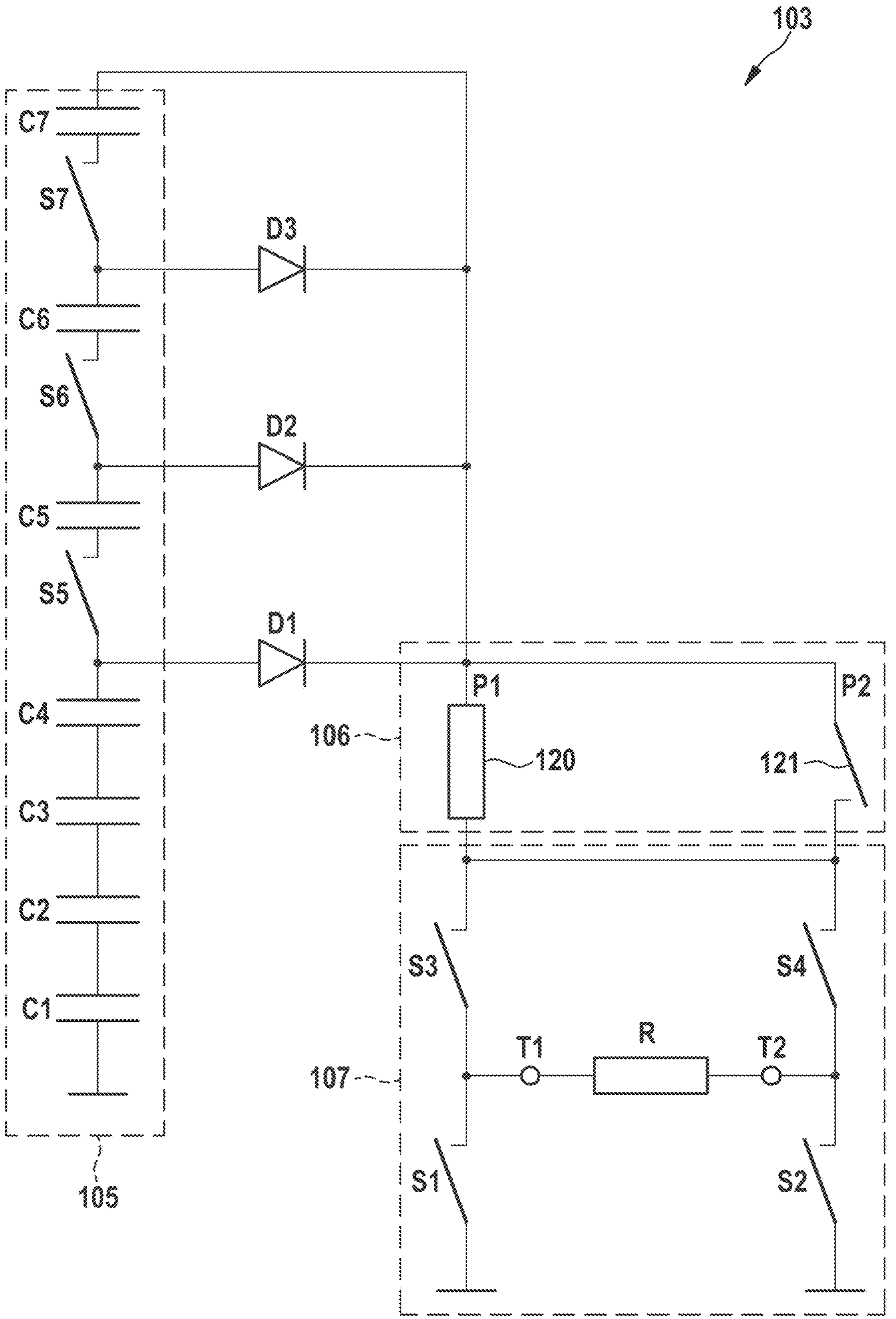
FIG. 8 shows yet another example of a shock generation circuitry for generating an output pulse, e.g., a fibrillation pulse.

Referring now to FIG. 8, in another embodiment the energy supply arrangement 105 and the output circuit 107 substantially matches the embodiment of FIG. 7. The embodiment of FIG. 8 however differs from the embodiment of FIG. 7 in the placement of the current limiting circuit 106.

Namely, in the embodiment of FIG. 8 the current limiting circuit 106 is not arranged in the path of capacitor C7 and switch S7, as in the embodiment of FIG. 7, but is arranged immediately prior to the output circuit 107. A current supplied from the energy supply arrangement 105 hence in any case, independent of whether none, some or all of the switches S5, S6 or S7 are closed, flows through the current limiting circuit 106, which again comprises a current limiting component 120 in a first path P1 and a switch 121 for selectively activating or deactivating the current limiting component 120 in a second path P2 in parallel to the first path P1.

The functionality of the current limiting circuit 106 in the embodiment of FIG. 8 otherwise is the same as described above in connection with the embodiments of FIGS. 3, 4, 6, and 7.

In the exemplary embodiment described above, a resistor of the current limiting circuit 106 may be used as a dump resistor for draining off energy which is not used for producing an output pulse.

For example, in the embodiment of FIG. 6 a dumping may be implemented by using a resistor implementing the current limiting component 120 as a dump resistor. For the dumping, switches S5, S6, S7 and switch 121 are switched to an open position. To perform the dumping, switch S8 is closed together with switches S1, S3 (or S2, S4).

In the embodiment of FIG. 7, a dumping is achieved by using a resistor implementing the current limiting component 120 as dump resistor. To perform the dump, the switch 121 is opened, and the switches S5, S6, S7 are closed together with switches S1, S3 (or S2, S4).

In the embodiment of FIG. 8, a dumping may be done by using a resistor implementing the current limiting component 120 as dump resistor. To perform the dump, the switch 121 is opened, and the switches S5, S6, S7 are closed together with switches S1, S3 (or S2, S4).

In the embodiment of FIG. 8, also a partial dump by dumping a remaining charge of capacitors C1-C4 only may be performed. To perform the partial dump, the switches

121, S5, S6, S7 are opened, and switches S1, S3 (or S2, S4) are closed. Subsequently, also the upper capacitors C5, C6, C7 may be dumped sequentially by sequentially closing the switches S5, S6 and S7. Herein, to prevent a reverse charging of the respective lower capacitor, the capacitors may be protected by a reverse oriented diode in parallel to the capacitor or a group of capacitors. "Reverse oriented" means that the anode of the diode is oriented towards the ground (or the normally negative charged plate of the capacitor).

The idea underlying the present invention is not limited to the embodiments described above, but may be implemented in an entirely different fashion.

An implantable cardioverter defibrillator device may comprise one or multiple leads, with one or multiple electrode poles arranged on each lead.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Non-transvenous implantable cardioverter defibrillator device
10 Generator device
100 Housing
101 Connection block
102 Processing circuitry
103 Shock generation circuitry
104 Energy storage (battery)
105 Energy supply arrangement
106 Current limiting circuit
107 Output circuit
11 Electrode lead
110 Lead body
111 Proximal end
112 Distal end
113, 114 Electrode pole
115 Shock electrode (coil)
120 Current limiting component
121 Switch device
122 Circuit component
123 Controllable component
124 Resistance
2 External device
A-D Reception vector
$A_1 \ldots A_n$ Amplitude
$B_1$, $B_2$ Distance
C1-C7 Capacitors
D1-D3 Diode
H Heart
$O_1 \ldots O_n$ Output pulse
P1, P2 Conducting path
R Resistance
S1-S8 Switches
T1, T2 Terminal
$W_1$, $W_2$, $W_n$ Pulse width

The invention claimed is:

1. An implantable cardioverter defibrillator device, comprising:
- a generator device comprising processing circuitry and shock generation circuitry; and
- at least one lead comprising a shock electrode for emitting an electrical output pulse;
- wherein said shock generation circuitry comprises an energy supply arrangement containing at least one energy storage device for supplying energy to form an output pulse, an output circuit for outputting said output pulse to the shock electrode, and a current limiting circuit arranged electrically in between the energy supply arrangement and the output circuit such that a current supplied from the energy supply arrangement flows through the current limiting circuit towards the output circuit;
- wherein said current limiting circuit comprises at least one current limiting component,
- wherein the current limiting circuit is controllable by the processing circuitry to modulate a current flowing through the current limiting circuit;
- wherein said processing circuitry is configured to control the current limiting circuit to generate a fibrillation pulse for emission by said shock electrode in order to induce a cardiac fibrillation state and to generate a defibrillation pulse for emission by said shock electrode in order to terminate a cardiac fibrillation state.

2. The implantable cardioverter defibrillator device according to claim 1, wherein the implantable cardioverter defibrillator device is a non-transvenous implantable cardioverter defibrillator device.

3. The implantable cardioverter defibrillator device according to claim 1, wherein said processing circuitry is configured to control the current limiting circuit to modulate said current flowing through the current limiting circuit to generate said fibrillation pulse according to a first modulation scheme and to generate said defibrillation pulse for emission by said shock electrode according to a second modulation scheme different than the first modulation scheme.

4. The implantable cardioverter defibrillator device according to claim 1, wherein the output circuit is formed by an H-bridge comprising switches to selectively form conduction paths for outputting said output pulse in a first polarity or in a second, opposite polarity.

5. The implantable cardioverter defibrillator device according to claim 1, wherein the energy supply arrangement comprises a multiplicity of energy storage devices functionally connected to at least one switching device, wherein the processing circuitry is configured to control the at least one switching device to supply energy for generating said output pulse using all of said multiplicity of energy storage devices or a combination of some of said multiplicity of energy storage devices.

6. The implantable cardioverter defibrillator device according to claim 1, wherein said processing circuitry is configured to control the current limiting circuit to set a voltage level of said output pulse using a pulse width modulation.

7. The implantable cardioverter defibrillator device according to claim 1, wherein the at least one current limiting component comprises a resistance, an inductance, or a semiconductor component.

8. The implantable cardioverter defibrillator device according to claim 1, wherein the current limiting circuit comprises a controllable component which is controllable by the processing circuitry.

9. The implantable cardioverter defibrillator device according to claim 1, wherein the current limiting circuit comprises a switch, wherein the current limiting component is arranged in a first path and the switch is arranged in a second path electrically in parallel to the first path.

10. The implantable cardioverter defibrillator device according to claim 1, further comprising a sensing arrangement for sensing electrocardiogram signals.

11. The implantable cardioverter defibrillator device according to claim 10, wherein at least one electrode pole of said sensing arrangement is arranged on said at least one lead.

12. The implantable cardioverter defibrillator device according to claim 10, wherein at least one electrode pole of said sensing arrangement is formed by a housing of said generator device.

13. The implantable cardioverter defibrillator device according to claim 10, wherein said sensing arrangement includes at least three electrode poles, the processing circuitry being configured to sense electrocardiogram signals using different pairs of electrode poles of said at least three electrode poles.

14. A method for operating an implantable cardioverter defibrillator device, said implantable cardioverter defibrillator device comprising a generator device and at least one lead having a shock electrode for emitting an electrical output pulse, the method comprising:

supplying, using an energy supply arrangement containing at least one energy storage device of shock generation circuitry of the generator device, energy to form an output pulse;

outputting, using an output circuit of said shock generation circuitry, said output pulse to the shock electrode;

controlling, using a processing circuitry of the generator device, a current limiting circuit comprising at least one current limiting component to modulate a current flowing through the current limiting circuit, wherein the current limiting circuit is arranged electrically in between the energy supply arrangement and the output circuit such that a current supplied from the energy supply arrangement flows through the current limiting circuit towards the output circuit; and controlling, using the processing circuitry of the generator device, the current limiting circuit to generate a fibrillation pulse for emission by said shock electrode in order to induce a cardiac fibrillation state and to generate a defibrillation pulse for emission by said shock electrode in order to terminate a cardiac fibrillation state.

* * * * *